(12) United States Patent
Noordhoek

(10) Patent No.: US 7,991,118 B2
(45) Date of Patent: Aug. 2, 2011

(54) SYSTEM AND METHOD FOR PROVIDING LATERAL AND FRONTAL X-RAY IMAGES OF A PATIENT

(75) Inventor: Niels Noordhoek, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 660 days.

(21) Appl. No.: 11/995,940

(22) PCT Filed: Jul. 12, 2006

(86) PCT No.: PCT/IB2006/052363
§ 371 (c)(1),
(2), (4) Date: Jan. 17, 2008

(87) PCT Pub. No.: WO2007/012990
PCT Pub. Date: Feb. 1, 2007

(65) Prior Publication Data
US 2010/0119042 A1    May 13, 2010

Related U.S. Application Data

(60) Provisional application No. 60/702,220, filed on Jul. 25, 2005.

(51) Int. Cl.
*H05G 1/58* (2006.01)
*H05G 1/02* (2006.01)
*H05G 1/64* (2006.01)

(52) U.S. Cl. .......................... 378/98; 378/115; 378/195
(58) Field of Classification Search ............... 378/4, 98, 378/114, 115, 195
See application file for complete search history.

(56) References Cited

U.S. PATENT DOCUMENTS

| 4,160,906 | A |   | 7/1979  | Daniels et al. |         |
|-----------|---|---|---------|----------------|---------|
| 5,020,089 | A | * | 5/1991  | Cramer et al.  | 378/196 |
| 5,448,614 | A | * | 9/1995  | Suzuki         | 378/115 |
| 5,740,222 | A |   | 4/1998  | Fujita et al.  |         |
| 6,149,592 | A | * | 11/2000 | Yanof et al.   | 600/427 |
| 7,835,498 | B2| * | 11/2010 | Bonfiglio et al. | 378/115 |
| 2004/0013239 | A1 |   | 1/2004 | Gregerson et al. |       |
| 2005/0116878 | A1 | * | 6/2005 | Warnberg       | 345/1.1 |
| 2006/0215817 | A1 | * | 9/2006 | Watanabe       | 378/114 |
| 2008/0030192 | A1 | * | 2/2008 | Fukui et al.   | 324/308 |

FOREIGN PATENT DOCUMENTS

DE    19726234    12/1998

\* cited by examiner

*Primary Examiner* — Irakli Kiknadze

(57) ABSTRACT

The present invention provides an imaging system (10) having a pedal-switching mechanism (14) for lateral and frontal imaging. The imaging system (10) is particularly useful for positioning an image-capturing device (18) with respect to a patient disposed on an imaging system (10) and may include a support member (20) configured to support a patient or object of interest, and a c-arm imaging equipment (12) configured to be removable to capture images in various directions.

30 Claims, 6 Drawing Sheets

SYSTEM AND METHOD FOR PROVIDING LATERAL AND FRONTAL X-RAY IMAGES OF A PATIENT

CROSS REFERENCE TO RELATED APPLICATIONS

This application claims the benefit of International Application Number PCT/IB2006/052363, filed Jul. 12, 2006, and U.S. Provisional Application Ser. No. 60/702,220, filed Jul. 25, 2005, which are incorporated herein in whole by reference.

The present invention relates to systems and methods for providing the measurement of X-ray images of a patient and, more particularly, a system and method that enables capturing of lateral and frontal X-ray images around a patient's body using a mono-plane device.

Medical biopsies and other medical procedures are frequently performed in conjunction with imaging equipment, such as CT (computer tomography) equipment, conventional x-ray equipment, magnetic resonance imaging equipment, or other imaging equipment used to collect a patient's data and display it to the clinician for diagnosis. One example is a mono-plane system capable of capturing X-ray pictures of a patient. Currently, using the mono-plane system, switching between lateral and frontal images of the patient is not feasible.

The shortcomings of the prior art noted above are addressed by the present inventive system that is operable to selectively take X-ray images in any application that requires frequent switching between frontal and lateral imaging, such as vertebroplasty, stent placemen, catheter navigation, screw placement, biopsies, drain placement, etc. The inventive system will enhance the workflow/user friendliness of any motorized monoplane system (i.e., URF, CV, and new generation Surgery systems) and save patients the medical cost associated with a lateral c-arm system.

The present invention provides a system having a pedal switch with a plurality of foot activatable switches and a single c-arm imaging equipment capable of capturing X-ray images of a patient. In operation, if a frontal pedal is pressed, the system quickly rotates to a frontal position and takes x-ray images of the patient, and when the lateral pedal is pressed, the system quickly rotates to a lateral position and continues to take x-ray images of the patient.

The present invention enhances the workflow, allowing the doctor to perform seamlessly and switch hands-free between a frontal and a lateral imaging, without having to fiddle with the table side controls with his or her hands.

According to the present invention, a pedal-switching device is capable of manipulating a c-arm imaging equipment with respect to a patient with at least one degree of freedom and preferably with multiple degrees of freedom. The pedal-switching device according to the present invention can be used with any type of imaging equipment, including computer tomography machines, magnetic resonance imaging machines, conventional x-ray machines, fluoroscopy systems, and ultrasonic imaging systems. However, it can also be used in applications not involving imaging.

The image may be displayed for the operator in any convenient manner, such as on a CRT or other type of electronic display, or in the form of a printed image on a sheet.

Details of the invention disclosed herein shall be described with the aid of the figures listed below, wherein.

For the purposes of clarity and simplicity, a detailed description of known functions and configurations incorporated herein will be omitted as it may make the subject matter of the present invention unclear.

Figure 1:
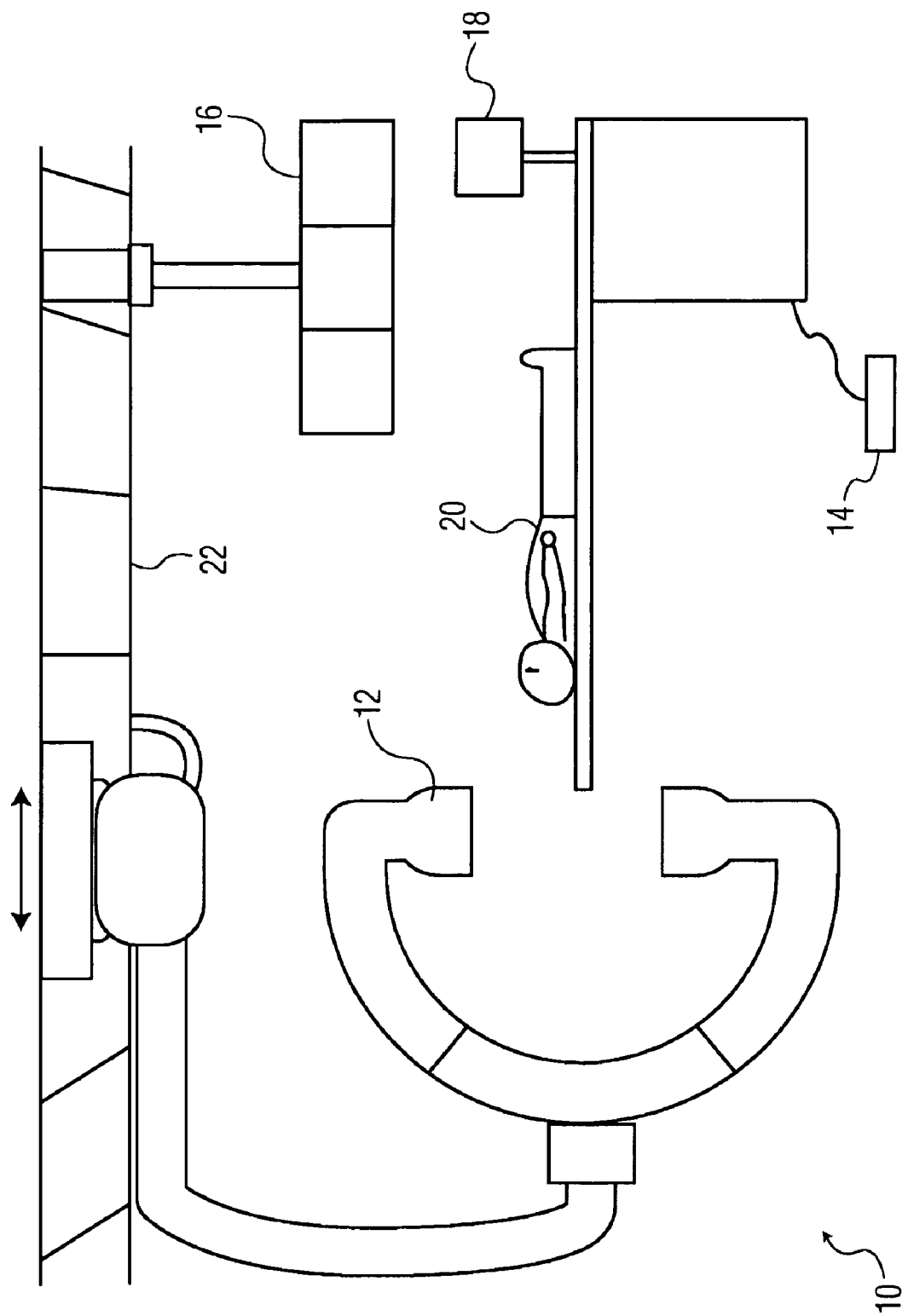
FIG. 1 is a diagram depicting an apparatus according to the present invention.

Referring to FIG. 1, an overview of an exemplary architecture for an imaging system 10 according to the present invention is shown. FIG. 1 particularly relates to the lateral and frontal imaging system 10, and is provided by way of illustrative and non-limitative example.

As shown, the imaging system 10 includes a c-arm 12, a pedal switch 14, a display 16, an imaging equipment 18 that may include an image detector/X-ray generator, and a table 20 for supporting a patient during imaging. Note that the c-arm 12 and the imaging equipment 18 may be integrated as a single-unit system. The system 10 further includes a guide system 22 for supporting and positioning the c-arm 12 or other medical devices with respect to a patient lying on the table 20. The table 20 is usually movable in its lengthwise direction to position the patient with respect to the c-arm 12, and the position of the table 20 can be selectively adjusted to direct the patient to a desired height.

It should be noted that the imaging system 10 according to the present invention can be used with other types of imaging devices and can also be employed separately from an imaging device. Further, mechanisms of the c-arm 12 in conjunction with the guide system 22 are well known in the art that can be performed in a variety of ways. As it is apparent to those having reasonable skill in this art, a discussion of the guide system and c-arm will be omitted. Mainly, the guide system 22 movably supports and engages the movement of the c-arm 12 around a patient using a well-known position mechanism, motor, and/or? actuator. For example, the c-arm 12 can be rotated using a rotary electric motor (not shown) or other type of actuators capable of producing rotation to face a particular direction about its lengthwise axis with respect to the interior of a patient's body. The motor may be equipped with a gear train if torque amplification is desired. A harmonic gear train is also suitable because it produces zero backlash and can provide smooth, precise control of the movement of the c-arm 12, but any other type of gear train may be used instead. If desired, the system 10 may be equipped with a position sensor for determining the position of the c-arm 12 in the lengthwise and/or circumferential direction of the table 20.

Figure 2:
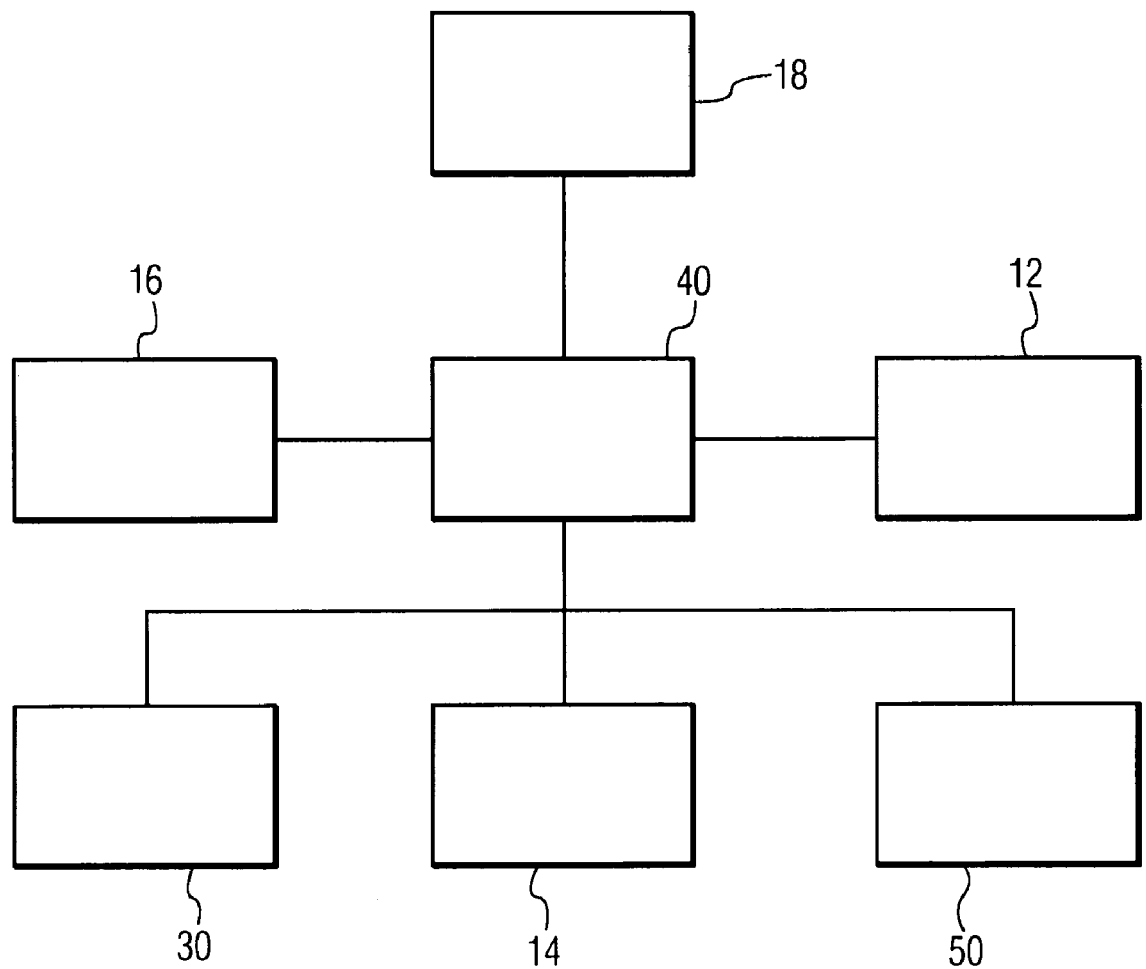
FIG. 2 is a block diagram depicting the apparatus shown in FIG. 1.

FIG. 2 illustrates a portion of the embodiment of FIG. 1 according to the present invention. The imaging system 10 according to the present invention may be equipped with a controller 40 for controlling the various actuators based on a program or commands from a human operator indicating the desired movements of the c-arm 12. The controller 40 may include an electronic controller, such as a general-purpose or special-purpose microcomputer, which receives input signals from position sensor 30 or from other sensing devices. The controller 40 also receives input signals from one or more input devices 14 by means of which the operator can provide the controller 40 with commands indicating the desired movement of the c-arm 12. The controller 40 may also be equipped with a memory 50 in which commands for controlling the c-arm can be stored.

In operation, based on input signals from the pedal switch 14 and the position sensor 30, the controller 40 generates control signals for the actuator so as to move the c-arm 12 in a desired manner and for the imaging equipment 18 to capture desired images. The controller 40 also sends control signals to the display 16 to provide a video or graphic image. The image may arrive in real-time from the acquisitions of an imaging device applied to a medical subject, or it may be retrieved from previous storage. Note that a wide variety of other input devices can be employed, such as a joystick, a haptic interface (an input device that can provide force feedback to the operator), a keyboard, a mouse, a digitizer, a computer glove, or a voice-operated controller. The controller 40 receives input signals from an operator, via the pedal switch 14, so as to move the c-arm 12 in a direction indicated by the operator. Activation of either the lateral or frontal button produces corresponding rotation of the c-arm 12 with respect to a patient. The pedal switch 14 is provided with a plurality of switch positions which permits the operator to activate the imaging equipment by means of foot manipulation. A detailed description of various pedal switches according to the teachings of the present invention will be described in detail hereinafter.

Figure 3A:
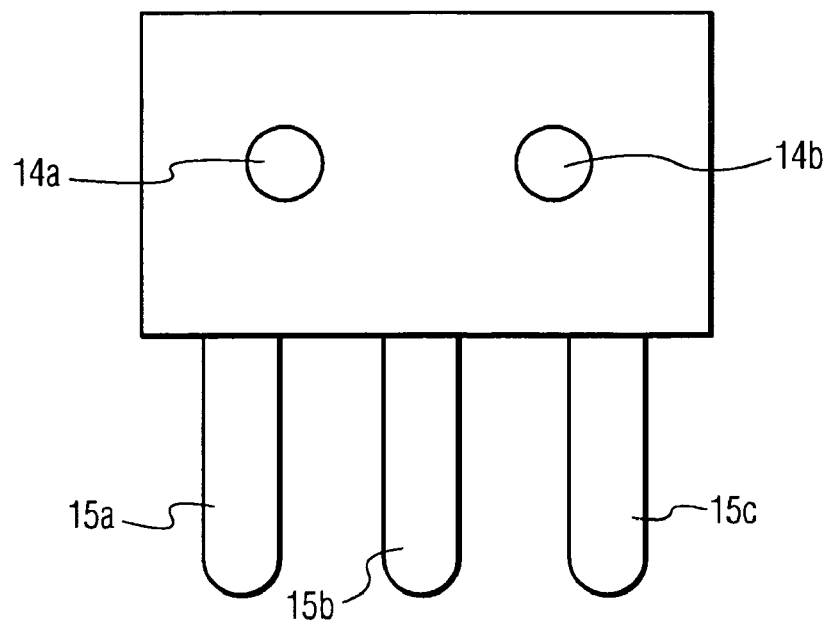
FIG. 3a -3f is a diagrammatic representation of a pedal switch of FIG. 1 in accordance with the present invention.

Referring to FIG. 3a, the pedal switch 14 may be provided with a lateral button 14a and a frontal button 14b and further equipped with a fluo 15a, exposure 15b, and single shot 15c buttons so as to enable the operator to press corresponding functions. The two buttons 14a and 14b may include a light to show the status of active mode. If the operator selects one of the lateral 14a or frontal 14b button, the orientation of c-arm 12 can be changed according to the activation of the button.

Figure 3B:
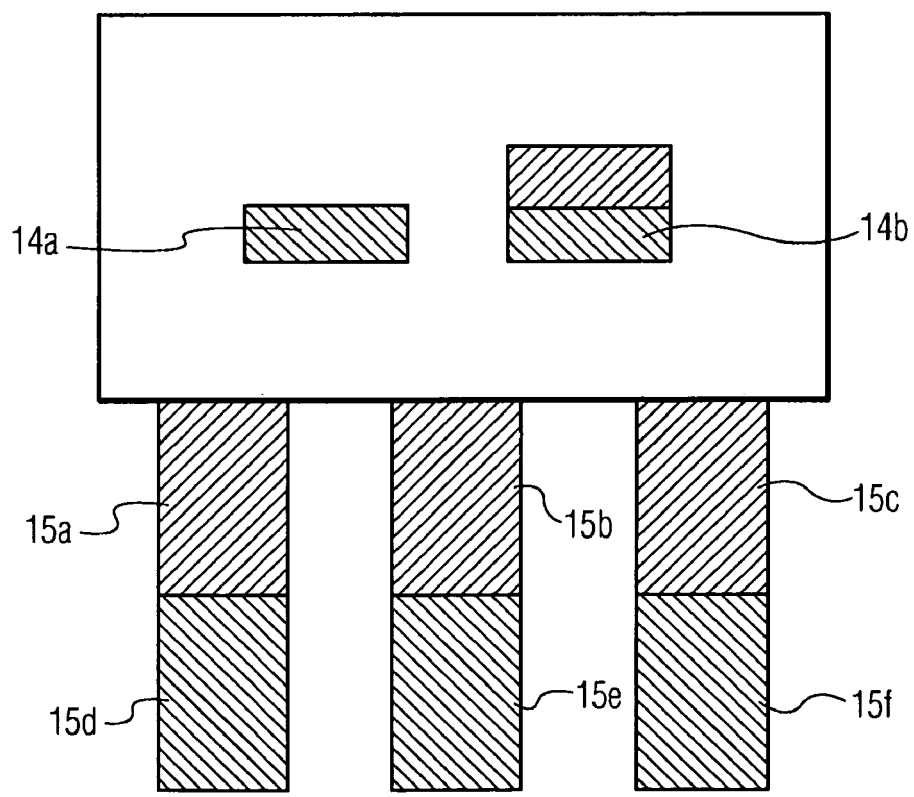

Referring to FIG. 3b, the pedal switch 14 may be provided with two sets of foot pedals, 15a-15c and 15d-15f. These two sets can be distinguished from each other with different colors. When one of the set 15a-15c buttons is activated, the lateral orientation can be achieved. When one of both sets, 15a-15c and 15d-15f, is pressed, the frontal orientation can be achieved.

Figure 3C:
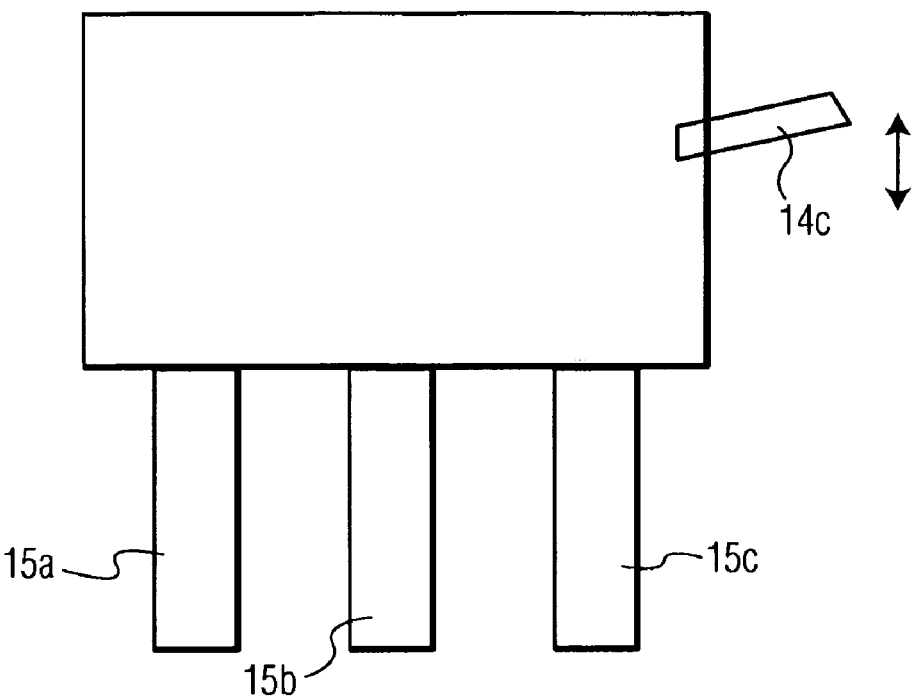

Referring to FIG. 3c, in addition to a fluo 15a, exposure 15b, and single shot 15c buttons, the pedal switch 14 may be equipped with a switch 14c to select either the frontal or lateral position.

Figure 3D:
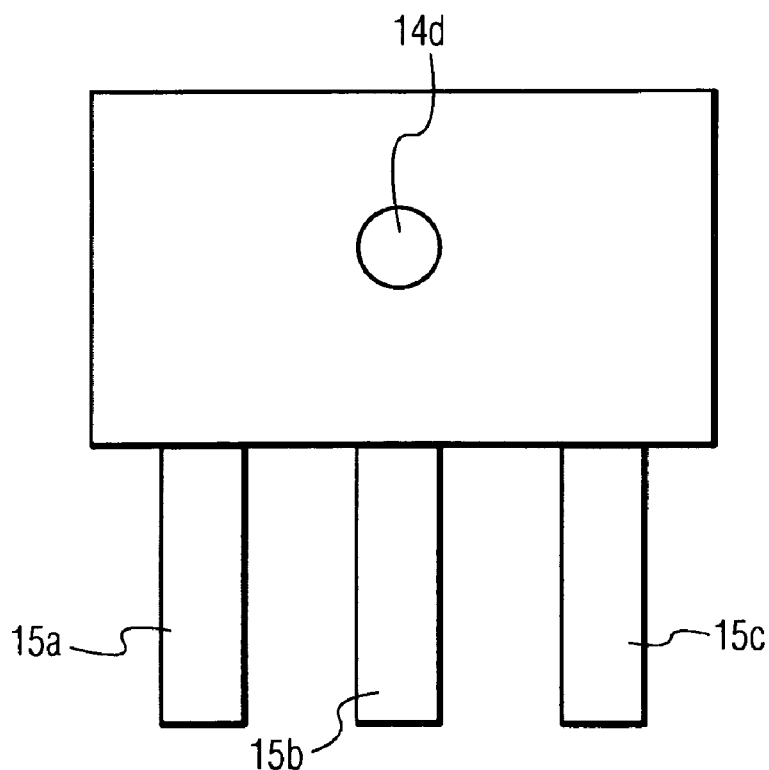

Referring to FIG. 3d, a single toggle switch 14d can be added so as to toggle between the frontal and lateral orientations. Colors of the pedals 15a-15c may change to reflect different modes, i.e., blue for frontal and red for lateral.

Figure 3E:
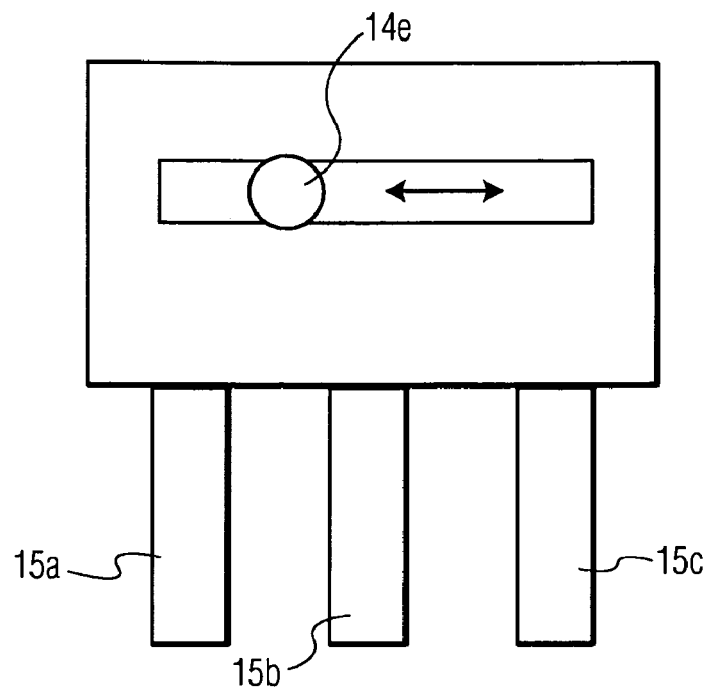

Referring to FIG. 3e, a slider 14e can be provided to indicate between frontal and lateral positions so as to determine the c-arm orientation under which x-ray exposure starts.

Figure 3F:
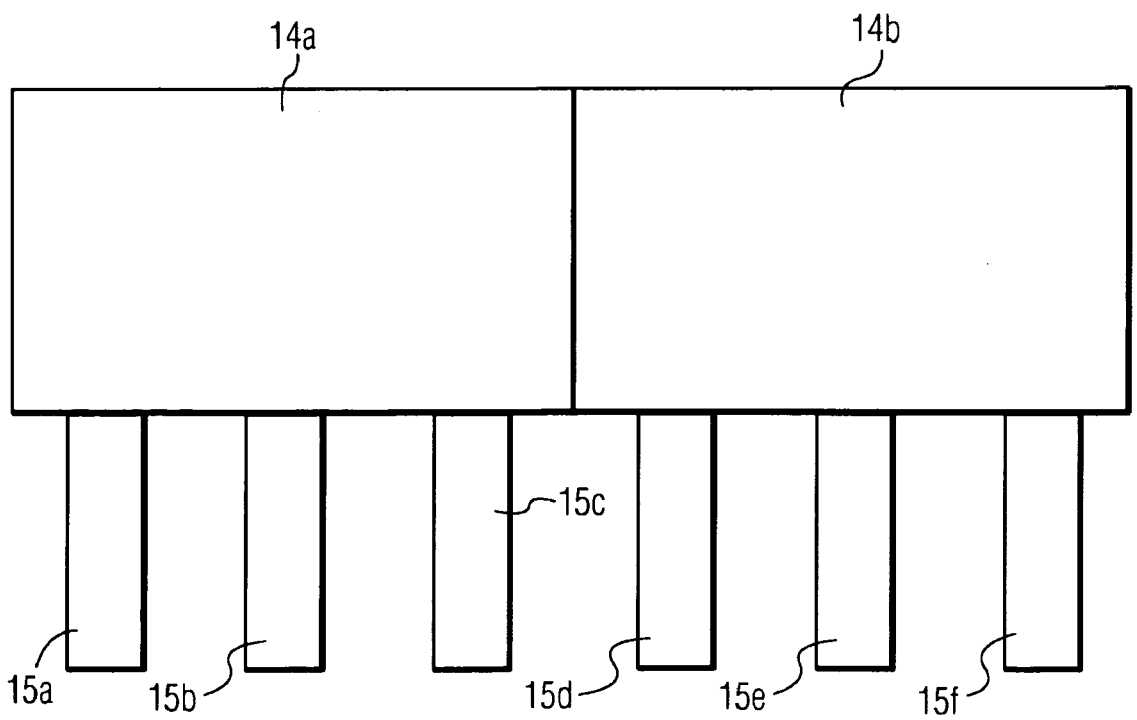

Referring to FIG. 3f, two sets of identical switches 14a and 14b can be provided, one for the lateral orientation and the other for the frontal orientation, so as to enable both orientations with the respective 15a-15c and 15d-15f buttons.

Figure 4:
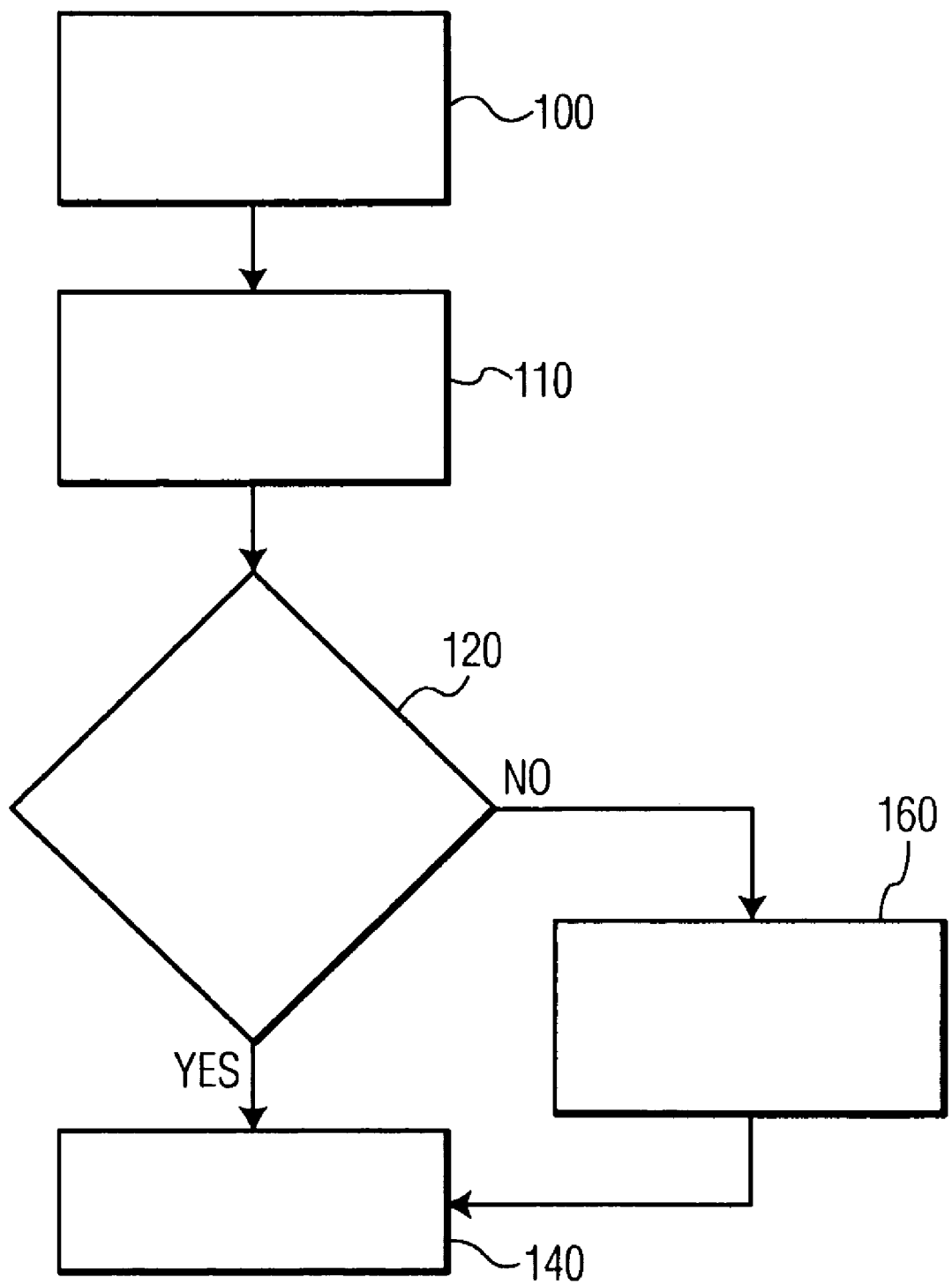
FIG. 4 is a flowchart showing the operation steps of the present invention.

FIG. 4 is a flow chart illustrating the operation steps of the imaging system 10 in accordance with the present invention.

Upon activation of a foot-pedal switch by an operator in step 100, the system determines the position of the c-arm 12 in step 110. If the position of c-arm 12 corresponds with the pedal pressed in step 120, x-ray images are generated in step 140. However, if the c-arm 12 position does not match the pedal pressed in step 120, the c-arm is rotated to match the position of the pedal pressed by the operator in step 160, and thereafter, an image is generated.

Having thus described embodiments of a system and method for providing at least two different degrees of imaging, it should be apparent to those skilled in the art that certain advantages of the system have been achieved. In particular, the pedal-switching device allows a human operator to activate the imaging equipment hands-free and complete imaging more rapidly while performing other tasks, thus increasing work efficiency.

While there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps that perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An imaging system used in a motorized monoplane system, comprising:
    a table for supporting a patient;
    a positioning mechanism movable around a patient lying on the table;
    a medical imaging device rotatably coupled to the positioning mechanism for selectively providing a lateral and a frontal imaging of the patient; and
    a programmable pedal switch having a plurality of foot-activatable switches that are each programmed to actuate both the lateral and frontal imaging of the patient.

2. The imaging device as claimed in claim 1, wherein the medical imaging device has a shape of an arc of a circle.

3. The imaging device as claimed in claim 1, further comprising a display.

4. The imaging device as claimed in claim 1, further comprising a position detector to detect the position of the patient relative to the medical-imaging device.

5. The imaging device as claimed in claim 1, wherein the positioning mechanism further includes guide rails to facilitate a transfer of the medical-imaging device around the patient.

6. The imaging device as claimed in claim 1, wherein the pedal switch is actuated by a human operator.

7. The imaging device as claimed in claim 1, wherein the pedal switch includes a lateral button and a frontal button activatable by an operator to change the orientation of the medical-imaging device according to the activation of the button.

8. The imaging device as claimed in claim 7, wherein the lateral and frontal buttons comprise a light to indicate the status of the activated button.

9. The imaging device as claimed in claim 1, wherein the pedal switch includes two sets of the foot-activatable switches distinguished by different colors from each other.

10. The imaging device as claimed in claim 1, wherein the pedal switch includes a switch to selectively actuate either the frontal or lateral imaging.

11. The imaging device as claimed in claim 1, wherein the pedal switch includes a single toggle switch so as to selectively toggle between the frontal and lateral imaging.

12. The imaging device as claimed in claim 1, wherein the pedal switch includes a slider switch so as to selectively actuate either the frontal or lateral imaging.

13. The system of claim 1, configured for the rotating to switch between said lateral and frontal imaging.

14. The system of claim 1, configured such that lateral and frontal imaging are non-simultaneous with each other.

15. The system of claim 1, configured such that the rotating is defined around an axis of rotation, the coupling occurring at said axis.

16. The system of claim 1, said device comprising, for said lateral and frontal imaging, a single X-ray generator rotatable respectively to a lateral and a frontal position.

17. A method for providing hands-free operation in capturing lateral and frontal images of a patient using an imaging device, the method comprising the steps of:
- detecting an activation of a pedal switch having a plurality of foot-activatable switches configured to select from among a plurality of modes of operation, said plurality of modes comprising a lateral mode and a frontal mode;
- determining whether a position of the imaging device corresponds to the selected mode; and
- if so, generating an image of the selected mode; otherwise, rotating the imaging device to activate the selected mode.

18. The method of claim 17, each of said foot-activatable switches being so configured.

19. An apparatus for providing hands-free operation in capturing lateral and frontal images of a patient in a motorized monoplane system, comprising:
- a processor;
- a memory, coupled to said processor, said memory being configured to allow the processor to:
  - provide an image for display;
  - use a pedal switch to select, from among modes of operation of the display, a lateral mode and a frontal mode; and
  - provide, respectively, lateral or frontal imaging by:
    - determining whether a position of the imaging device corresponds to the selected mode;
    - if so, generating an image of the selected mode; and,
    - if not, rotating said imaging device to match the selected mode and then generating an image.

20. The apparatus as claimed in claim 19, wherein the imaging device has the shape of an arc of a circle.

21. The apparatus as claimed in claim 19, further comprising a display.

22. The apparatus as claimed in claim 19, wherein the pedal switch is actuated by a human operator.

23. The apparatus as claimed in claim 19, wherein the pedal switch includes a lateral button and a frontal button activatable by an operator to change the orientation of a medical-imaging device according to the activation of the button.

24. The apparatus as claimed in claim 19, wherein the lateral and frontal buttons comprise a light to indicate the status of the activated button.

25. The apparatus as claimed in claim 19, wherein the pedal switch includes two sets of the foot activatable switches distinguished by different colors from each other.

26. The apparatus as claimed in claim 19, wherein the pedal switch includes a switch to selectively actuate either the frontal or lateral imaging.

27. The apparatus as claimed in claim 19, wherein the pedal switch includes a single toggle switch so as to selectively toggle between the frontal and lateral imaging.

28. The apparatus as claimed in claim 19, wherein the pedal switch includes a slider switch so as to selectively actuate either the frontal or lateral imaging.

29. The apparatus as claimed in claim 19, wherein the pedal switch includes two sets of the foot activatable switches, one set for actuating the frontal imaging and the other for the lateral imaging.

30. An apparatus for providing a hands-free operation of capturing lateral and frontal images of a patient in a motorized monoplane system, comprising:
- a processor;
- a memory, coupled to said processor, said memory being configured to allow the processor to:
- provide an image for display;
- select from among at least two modes of operation of the display, in particular a lateral mode and a frontal mode using a pedal switch; and
- provide one of a lateral or frontal imaging by rotating an imaging device to match the selected mode, wherein the pedal switch includes a plurality of foot-activatable switches, each of the foot-activatable switches programmed to actuate the lateral and frontal imaging of the patient.

\* \* \* \* \*